US009144799B2

(12) United States Patent
Rose et al.

(10) Patent No.: US 9,144,799 B2
(45) Date of Patent: Sep. 29, 2015

(54) MODULAR MICROFLUIDIC SYSTEM FOR BIOLOGICAL SAMPLE PREPARATION

(75) Inventors: Klint A. Rose, Alviso, CA (US); Raymond P. Mariella, Jr., Danville, CA (US); Christopher G. Bailey, Pleasanton, CA (US); Kevin Dean Ness, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 775 days.

(21) Appl. No.: 12/943,677

(22) Filed: Nov. 10, 2010

(65) Prior Publication Data

US 2011/0124098 A1    May 26, 2011

Related U.S. Application Data

(60) Provisional application No. 61/264,148, filed on Nov. 24, 2009.

(51) Int. Cl.
| | |
|---|---|
| *C12M 1/33* | (2006.01) |
| *C12M 3/08* | (2006.01) |
| *B01L 3/00* | (2006.01) |
| *B03C 5/02* | (2006.01) |
| *G01N 35/00* | (2006.01) |

(52) U.S. Cl.
CPC ..... *B01L 3/502761* (2013.01); *B01L 3/502753* (2013.01); *B03C 5/026* (2013.01); *B01L 2200/027* (2013.01); *B01L 2200/04* (2013.01); *B01L 2300/0681* (2013.01); *B01L 2400/0436* (2013.01); *B01L 2400/0439* (2013.01); *B03C 2201/26* (2013.01); *G01N 2035/00326* (2013.01)

(58) Field of Classification Search
CPC ............... B01L 3/502753; B01L 3/502761; B01L 2200/027; B01L 2200/04; B01L 2400/0436; B01L 2400/0439; B01L 2300/0681; B03C 5/026; B03C 2201/26; G01N 2035/00326
USPC ...................................................... 435/306.1
See application file for complete search history.

(56) References Cited

U.S. PATENT DOCUMENTS

| | | | |
|---|---|---|---|
| 6,352,838 B1 | 3/2002 | Krulevitch | |
| 6,730,204 B2 | 5/2004 | Mariella, Jr. | |
| 6,761,811 B2 | 7/2004 | Mariella, Jr. | |
| 2002/0139674 A1* | 10/2002 | Mariella, Jr. | 204/547 |
| 2008/0227185 A1* | 9/2008 | Schonfeld et al. | 435/287.2 |
| 2009/0194420 A1 | 8/2009 | Mariella, Jr. | |
| 2010/0261612 A1* | 10/2010 | Young | 506/7 |

OTHER PUBLICATIONS

Raymond Mariella, Jr., "Sample Preparation: The Weak Link in Microfluidics-Based Biodetection". Biomed Microdevices (2008) 10:777-784. Published online: May 16, 2008. © Springer Science + Business Media, LLC 2008.

\* cited by examiner

*Primary Examiner* — Michael Hobbs
(74) *Attorney, Agent, or Firm* — Eddie E. Scott

(57) ABSTRACT

A reconfigurable modular microfluidic system for preparation of a biological sample including a series of reconfigurable modules for automated sample preparation adapted to selectively include a) a microfluidic acoustic focusing filter module, b) a dielectrophoresis bacteria filter module, c) a dielectrophoresis virus filter module, d) an isotachophoresis nucleic acid filter module, e) a lyses module, and f) an isotachophoresis-based nucleic acid filter.

2 Claims, 4 Drawing Sheets

MODULAR MICROFLUIDIC SYSTEM FOR BIOLOGICAL SAMPLE PREPARATION

CROSS-REFERENCE TO RELATED APPLICATIONS

The present application claims benefit under 35 U.S.C. §119(e) of U.S. Provisional Patent Application No. 61/264,148 filed Nov. 24, 2009 entitled "Modular Microfluidic System for Biological Sample Preparation," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to sample preparation and more particularly to a modular microfluidic system for biological sample preparation.

2. State of Technology

Nearly all biological assays require front end sample preparation to process a complex sample such as blood, saliva, or urine and extract the biological material of interest. Benchtop techniques, such as membrane filtration, centrifugation, and chemical methods, have demonstrated preparation of biological materials from a wide range of complex fluids. Robust, automated sample preparation, however, remains an open challenge. The automated sample preparation system of the present invention will perform the critical step of preparing complex samples from environmental aerosol collectors for whole bacteria, intact virus, RNA, DNA, and protein testing by a variety of downstream assays. The automated sample preparation system of the present invention goes beyond solid-phase extraction methods and offers distinct advantages over traditional approaches including: 1) significant reductions in genomic and protein background concentrations via bioparticle fractionation; 2) reagentless processing, requiring only simple, stable buffers; 3) compatibility with a large range of input sample solution properties; 4) high recovery efficiency due to low-surface area; 5) high-throughput (order 100 µL/min) with the ability to handle a large range of volumes (10 µL to >1 mL); and 6) straightforward integration into a small, automated, fieldable system.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a series of lab-on-a-chip modules for an automated sample preparation of complex clinical and environmental biological samples. The present invention provides a reconfigurable modular microfluidic system for preparation of a biological sample including a series of reconfigurable modules for automated sample preparation adapted to selectively include a) a microfluidic acoustic focusing filter module, b) a dielectrophoresis bacteria filter module, c) a dielectrophoresis virus filter module, d) an isotachophoresis nucleic acid filter module, e) a lysis module, and f) an isotachophoresis-based nucleic acid filter.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
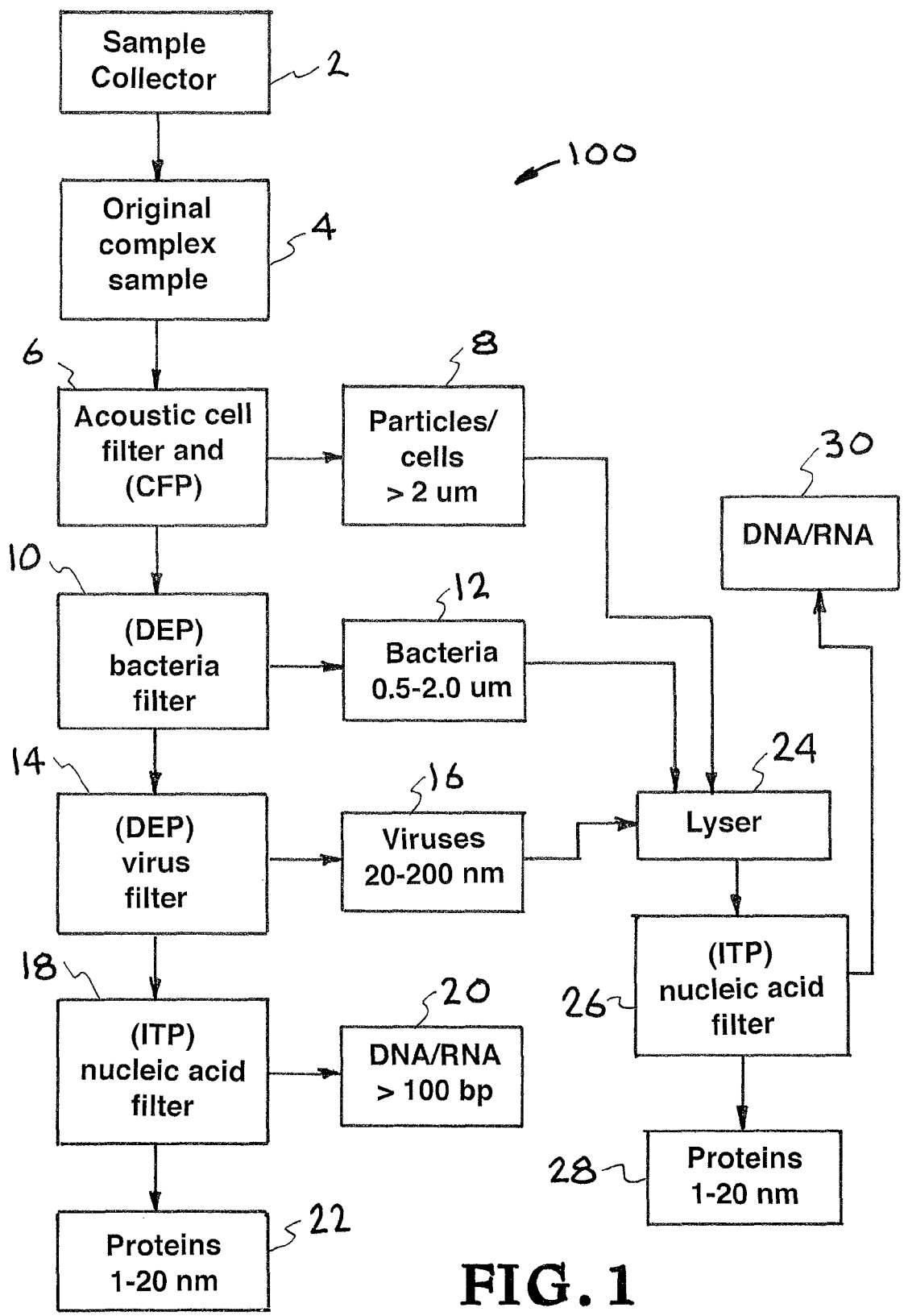
FIG. 1 illustrates one embodiment of an automated sample preparation system constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a series of lab-on-a-chip modules for an automated sample preparation of complex clinical and e environmental biological samples (e.g. blood, nasal washes, air collectors, etc). These devices are based on microfluidic filters which we use acoustic focusing, dielectrophoresis (DEP), and isotachophoresis (ITP) as a replacement for physical filters to separate analytes based on size or electric charge. A fourth module lyses separated cells to provide access to the nucleic acids or proteins within the cell. Each microfluidic chip is packaged into a integrated module that includes the necessary pumps, valves, and electronics to load the sample, pump it through the microfluidic chip, and drive the piezoelectric or electrodes required for the specific chip. Each module can be either standalone (e.g. separate only cells from a sample), or connected together in a serial layout to match the needs of the downstream assay. This approach will enable the user to capture and bin cells, bacteria. viruses, proteins, and DNA/RNA for further analysis by existing and future assays. This sample preparation approach is advantageous because it is reagentless and nearly loss-less with throughputs on the order of 100 μL/min. The modules are also easily integrated into a fieldable system

EXAMPLES

Referring now to the drawings and in particular to FIG. 1, one embodiment of an automated sample preparation system constructed in accordance with the present invention is illustrated. The automated sample preparation system is designated generally by the reference numeral 100. The automated sample preparation system 100 includes a series of microfluidic chip based modules. The automated sample preparation system 100 will accept a complex, environmental aerosol collector sample and selectively extract and bin the cells, bacteria, viruses, and free-floating nucleic acids. After removing these components, the remaining effluent will contain primarily proteins. Each binned sample (e.g. bacteria) can then either be transported out of the system 100 for culture analysis or immunoassay testing, or it can be processed through our lysing module to release the nucleic acids and proteins. The lysate can be processed through an additional nucleic acid filter to extract the desired DNA/RNA for PCR, sequencing, or SNP analysis while also collecting the remaining proteins for immunoassays. The automated sample preparation system 100 enables the user to selectively remove unwanted biological content from the sample without losing the desired target due to mismatched specificity, as in an affinity- or enzymatic-based approach.

Referring again to FIG. 1, a flow chart illustrates the automated sample preparation system (ASPS) 100. The (ASPS) 100 is composed of a series of micro fluidic chip based modules. This integrated system will accept a complex sample. The sample collector 2 can be an aerosol collector or the sample can be introduced manually to the system. A large verity of different sample can be processed by this system such as the afore mentioned aerosol sample as well as blood, saliva, urine or almost any fluid containing particles of interest to the user of this device. The original complex sample 4 now enters the integrated modular system 100 at the acoustic cell filter and (CFP) 6 here particles/cells larger than 2 um are separated and sent to a bin 8. The binned sample (e.g. particles/cells) can then either be transported out of the system for culture analysis or immunoassay testing, or can be processed through the lysing module 24 to release the nucleic acids and proteins. The lysate can be processed through an additional nucleic acid filter 26 to extract the desired DNA/RNA for PCR, sequencing, or SNP analysis while also collecting the remaining proteins 28 for immunoassays. The original complex sample 4 can also be processed by the integrated modules 10 and 14. The module 10 is a dielectrophoresis bacteria filter and bacteria of 0.5-2.0 um will be stored in bin 12. From bin 12 the bacteria can be processed in the same manner as the particles from bin 8. The original complex sample 4 may also enter module 14 which is an dielectrophoresis virus filter and the separated particles (viruses' 20-200 nm) will be stored in bin 20 and again these particles can be processed as were those in bin 8. The original complex sample 4 can now enter module 18 which is an isotachophoresis nucleic acid filter where DNA/RNA greater than 100 bp will be stored in bin 20 available for further analysis. The remaining proteins 22 are also collected for immunoassay.

The original complex sample is moved through the integrated modular system by a system of valves and pumps which are not shown. The modular system can be configured in different ways to meet the needs of the end user. Once the sample is loaded in the single input line, the software will control the individual modules as well as the system of valves and pumps to process the sample through the necessary filters.

The automated sample preparation system 100 provides an microfluidic automated sample preparation system 100 for preparation of biological samples including a series of configurable modules for automated sample preparation adapted to selectively utilize a microfluidic acoustic focusing filter module, a dielectrophoresis filter module, an isotachophoresis filter module, and alyses module. The automated sample preparation system 100 includes the necessary pumps, valves, and electronics to load the sample, pump it through the microfluidic chip, and drive the piezoelectric or electrodes required for the specific chip. Each module can be either standalone (e.g., separate only cells from a sample), or connected together in a serial layout to match the needs of the downstream assay.

Applicants' microfluidic virtual filter modules and integrated system 100 is capable of accepting and processing a complex aerosol collector sample, binning each class of analyte. then lysing the desired cells, bacteria, or viruses to capture their nucleic acids or proteins. Unlike high-surface area membranes or columns, which may cause sample loss due to adsorption or reduced elution efficiency, our low-surface-area "virtual filters" use engineered electric, acoustic, and hydrodynamic fields to remove and bin desired analytes. This technique will enable our system to retain >50% of the target DNA, RNA, and protein content from the original sample. Also, our preliminary results indicate that the microfluidic filters maintain the viability of the biological material as it passes through the system, and so enable downstream culture analysis or immunoassay detection.

The automated sample preparation system 100 can be used either as a subsystem placed directly in-line between an aerosol collector and downstream detection system or as a stand-alone system with manual transfer of the sample to and from the collection and detection systems. In either case, the end-user will operate this system primarily through the system-level software. Once the sample is loaded in the single input line, the software will control the individual modules as well as the system valves and pumps to process the sample through the necessary filters.

Figure 2A:
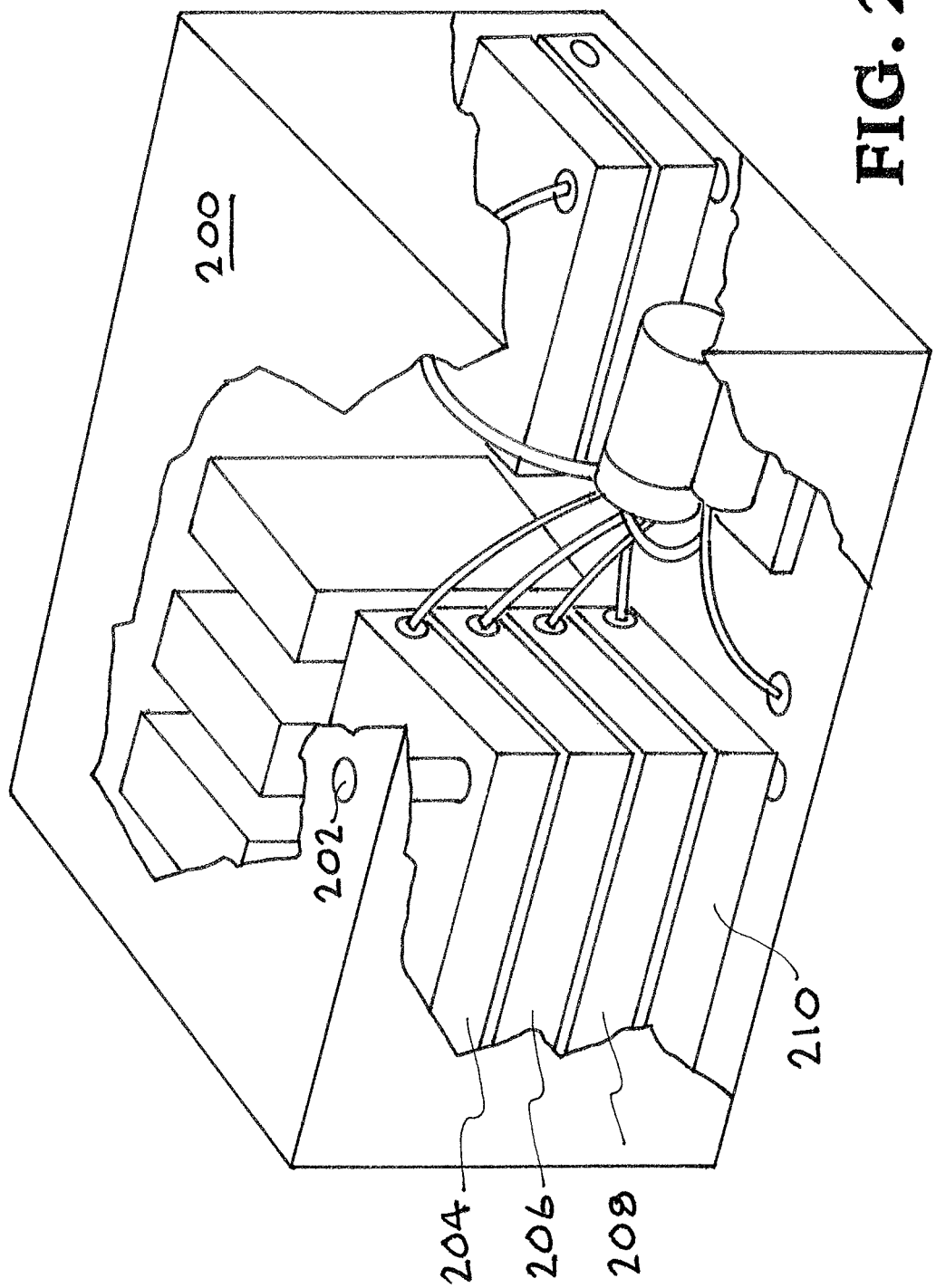
FIGS. 2A, 2B, and 2C illustrate another embodiment of an automated sample preparation system constructed in accordance with the present invention
Figure 2B:
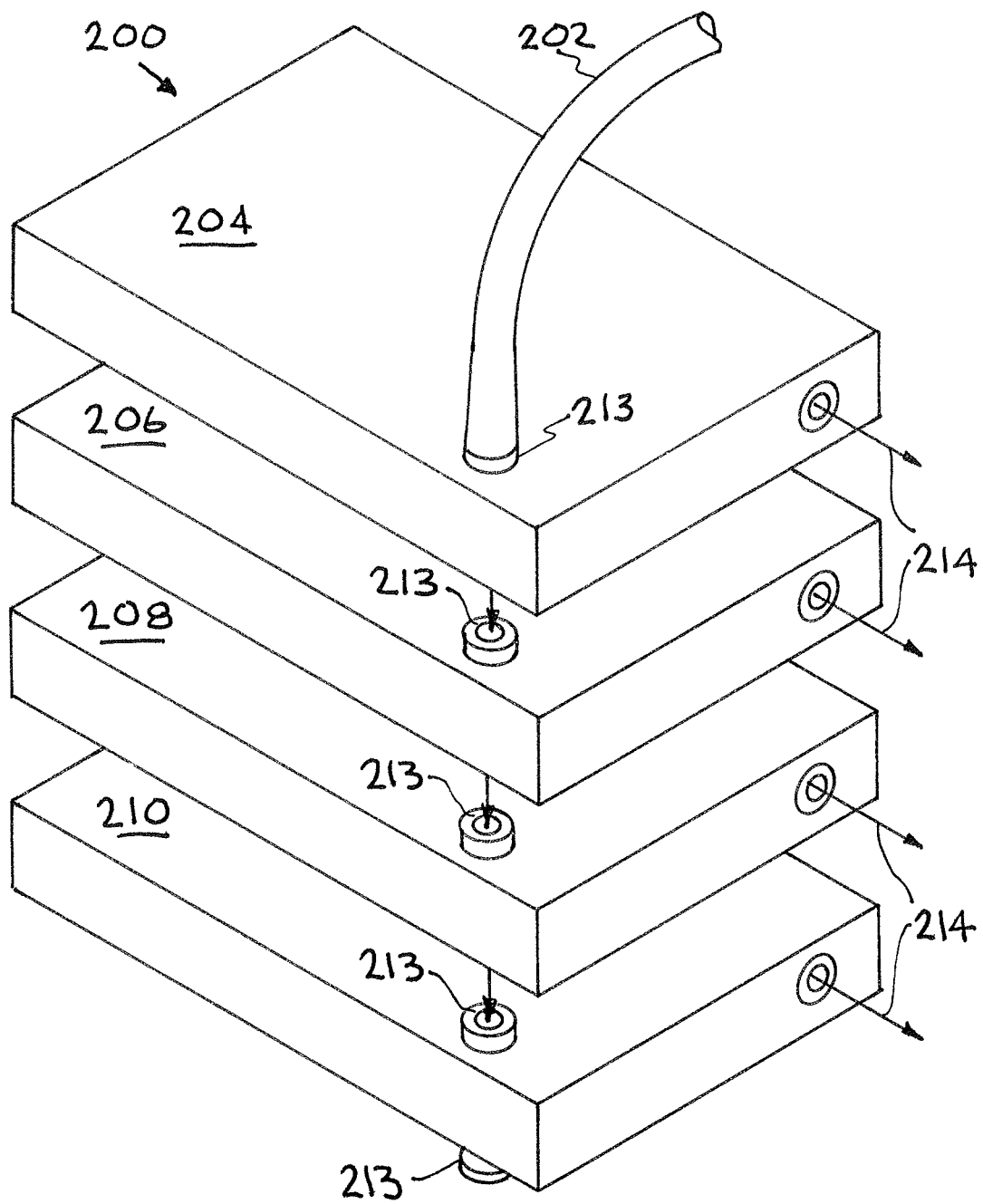
Figure 2C:
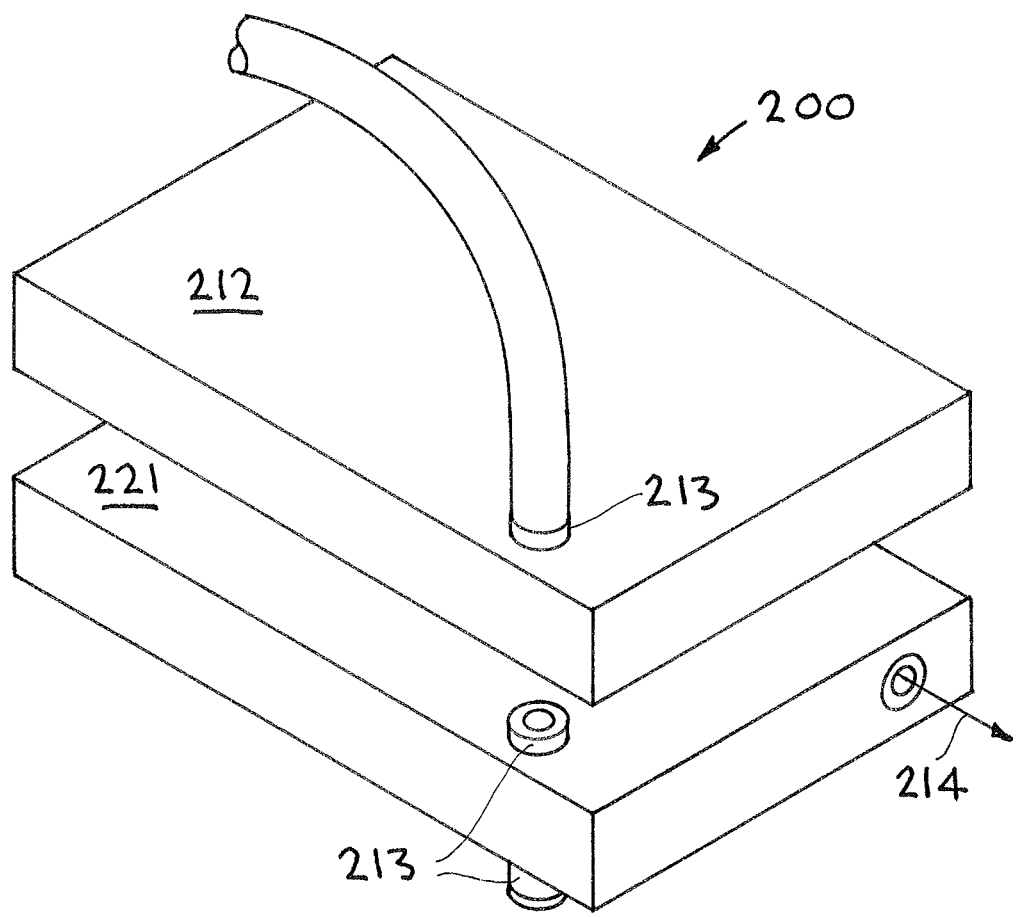

Referring again to the drawings and in particular to FIGS. 2A, 2B, and 2C, another embodiment of an automated sample preparation system constructed in accordance with the present invention is illustrated. This embodiment of an automated sample preparation system is designated generally by the reference numeral 200. The system 200 is a series of lab-on-a-chip modules for a automated sample preparation of complex clinical and e environmental biological samples (e.g. blood, nasal washes, air collectors, etc). These devices are based on microfluidic filters which use acoustic focusing, dielectrophoresis (DEP), and isotachophoresis (ITP) as a replacement for physical filters to separate analytes based on size or electric charge. A fourth module lyses separated cells to provide access to the nucleic acids or proteins within the cell. Each microfluidic chip is packaged into an integrated module that includes the necessary pumps, valves, and electronics to load the sample, pump it through the microfluidic chip, and drive the piezoelectric or electrodes required for the specific chip. Each module can be either standalone (e.g. separate only cells from a sample), or connected together in a serial layout to match the needs of the downstream assay. The system 200 enables the user to capture and bin cells, bacteria, viruses, proteins, and DNA/RNA for further analysis by existing and future assays. The system 200 is advantageous because it is reagentless and nearly loss-less with throughputs on the order of 100 µL/min. The independent modules are also easily integrated into a fieldable system.

The sample preparation modules of the system 200 are designed to be applied to all biological sample preparation in which generic biological partical types, e.g. cells, bacteria, DNA/RNA, need to be removed from a sample. The modules can be used individually or in series to provide the user the capabilities needed to prepare assays for their specific sample. Therefore, the system 200 can be used in medical applications as a front end cleanup of blood, urine, saliva, or other fluids. The system 200 can be used as the front end system in biological research applications such as sequencing, PCR, microarray identification, or a wide range of other assays. The relatively compact size of the module system also enables integration of this sample preparation into fieldable biodetection systems.

The automated sample preparation system 200 includes a series of microfluidic chip based modules. This integrated system will accept a complex, environmental aerosol collector sample and selectively extract and bin the cells, bacteria, viruses, and free-floating nucleic acids. Alternatively the sample can be introduced manually to the system or the system 200 can receive as sample from other sample collection systems. After removing these components, the remaining effluent should contain primarily proteins. Each binned sample (e.g. bacteria) can then either be transported out of the system for culture analysis or immunoassay testing, or it can be processed through our lysing module to release the nucleic acids and proteins. The lysate can be processed through an additional nucleic acid filter to extract the desired DNA/RNA for PCR, sequencing, or SNP analysis while also collecting the remaining proteins for immunoassays. The automated sample preparation system 200 enables the user to selectively remove unwanted biological content from the sample without losing the desired target due to mismatched specificity, as in an affinity- or enzymatic-based approach.

Referring now to FIGS. 2A and 2B, the sample from the sample collector is loaded into the automated sample preparation system 200 through the sample input unit 202. The system 200 pumps the sample into the first module, the acoustic cell filter 204. In this module the large cells (tree, grass insect, avian, and mammalian) as well as any non-biological particles larger than 2 m are removed with at least 98% efficiency. Particles smaller than −2 µm, including both the non-threat and target bacteria, pass through the acoustic filter 204 at a minimum recovery of 90%. The sample then continues to the second module, the dielectrophoresis bacteria filter 206, where both non-threat and target bacteria are extracted with at least 98% efficiency. Note that most large cell contaminants that were not extracted in the acoustic filter (2%) should be extracted with the bacteria at this step. The sample then continues to the third module, the dielectrophoresis virus filter 208 and the fourth module, the isotachophoresis nucleic acid filter 210.

Referring now to FIG. 2B, the system 200 is a lab-on-a-chip apparatus for preparing a biological sample that includes a chip, a series of lab-on-a-chip modules including a microfluidic acoustic focusing filter of lab-on-a-chip module, a dielectrophoresis bacteria filter of lab-on-a-chip module, a dielectrophoresis virus filter module, an isotachophoresis nucleic acid filter of lab-on-a-chip module, a lysis of lab-on-a-chip module, and an isotachophoresis-based nucleic acid filter of lab-on-a-chip module, wherein the apparatus for preparing a biological sample can be configured to include one or more of the series of modules including a microfluidic acoustic focusing filter of lab-on-a-chip module, a dielectrophoresis bacteria filter of lab-on-a-chip module, a dielectrophoresis virus filter of lab-on-a-chip module, an isotachophoresis nucleic acid filter of lab-on-a-chip module, lysis of lab-on-a-chip module, and an isotachophoresis-based nucleic acid filter module to comprise the of lab-on-a-chip apparatus for preparing a biological sample. The microfluidic acoustic focusing filter of lab-on-a-chip module, the dielectrophoresis bacteria filter of lab-on-a-chip module, the dielectrophoresis virus filter module, the isotachophoresis nucleic acid filter of lab-on-a-chip module, the lysis of lab-on-a-chip module, and the isotachophoresis-based nucleic acid filter of lab-on-a-chip module are connected together by connectors 213. The microfluidic acoustic focusing filter of lab-on-a-chip module, the dielectrophoresis bacteria filter of lab-on-a-chip module, the dielectrophoresis virus filter module, the isotachophoresis nucleic acid filter of lab-on-a-chip module, the lysis of lab-on-a-chip module, and the isotachophoresis-based nucleic acid filter of lab-on-a-chip module each include an outlet flow 214. The system 200 provides a reconfigurable modular microfluidic system for preparation of a biological sample. The system 200 includes a series of reconfigurable modules for automated sample preparation adapted to selectively include a) a microfluidic acoustic focusing filter module, b) a dielectrophoresis bacteria filter module, c) a dielectrophoresis virus filter module, d) an isotachophoresis nucleic acid filter module, e) a lyses module, and f) an isotachophoresis-based nucleic acid filter. The microfluidic acoustic focusing filter of lab-on-a-chip module, the dielectrophoresis bacteria filter of lab-on-a-chip module, the dielectrophoresis virus filter module, the isotachophoresis nucleic acid filter of lab-on-a-chip module, the lysis of lab-on-a-chip module, and the isotachophoresis-based nucleic acid filter of lab-on-a-chip module are connected together by connectors 213.

Referring now to FIG. 2C, the system 200 then pumps the bacterial sample into the lysis module 212 to free at least 75% of the intracellular DNA for analysis. This lysed sample then passes through the isotachophoresis-based nucleic acid filter 214 which separates the DNA from other lysate material at 98% efficiency and concentrates it for analysis.

Nearly all biological assays require front end sample preparation to process a complex sample such as blood, saliva, or urine and extract the biological material of interest. Benchtop techniques, such as membrane filtration, centrifugation, and chemical methods, have demonstrated preparation of biological materials from a wide range of complex fluids. Robust, automated sample preparation, however, remains an open challenge. The automated sample preparation system 200 will perform the critical step of preparing complex samples from environmental aerosol collectors for whole bacteria, intact virus, RNA, DNA, and protein testing by a variety of downstream assays. The system 200 goes beyond solid-phase extraction methods and offers distinct advantages over prior art approaches including: 1) significant reductions in genomic and protein background concentrations via bioparticle fractionation; 2) reagentless processing, requiring only simple, stable buffers; 3) compatibility with a large range of input sample solution properties; 4) high recovery efficiency due to low-surface area; 5) high-throughput (order 100 µLJmin) with the ability to handle a large range of volumes (10 µL to >1 mL); and 6) straight-forward integration into a small, automated, fieldable system.

Applicants have completed experiments demonstrating the efficacy of the system 200 ITP-based selective extraction of extracellular DNA from a complex sample. Applicants collected a nasal rinse from a healthy patient using a commercial saline rinse solution (Ayr) and performed a series of ITP based extractions including negative controls.

Applicants fabricated an initial prototype of the system 200's ITP-based FFE extraction system and completed a series of experiments demonstrating its efficacy. Using this prototype, Applicants performed a set of experiments where Applicants verified focusing of DNA.

Applicants performed a "classical" on-chip ITP assay (separation and focusing along the same axis as fluid flow) with a sample containing MS2 bacteriophage and a 1 kbp ladder. Applicants labeled MS2 with alexa fluor 594 red fluorescent dye (Invitrogen) yielding a mixture of tagged viruses and free dye. Applicants showed ITP separation results. This experiment demonstrates the potential of ITP to specifically purify and fractionate viruses from DNA and proteins. A spacer solution focuses between the virus and a zone containing both tagged DNA and the labeling byproducts. The choice of this spacer is based on the known mobilities of the MS2 bacteriophage and DNA. Based on these results, Applicants also performed similar experiments demonstrating the ability of our FFE ITP device to focus, fractionate, and extract DNA from a virus stream of MS2 bacteriophages.

Module Descriptions

One embodiment of the integrated system of the present invention is comprised of five modules to fractionate cells, bacteria, extracellular viruses, and nucleic acids and then lyre the fractionated materials. Each module includes 1) Applicants' proposed Protein Recovery by Elimination of Other Constituents Because proteins do not offer an ideal, generic property that enables fractionation of all potential target proteins from a solution, our approach is to remove all other major constituents from the sample leaving primarily proteins in the output solution. The final protein content in the sample will depend on the recovery efficiency through all upstream modules. Based on 90% recovery through each module and 75% lysing efficiency, the total protein recovery should exceed 65% for extracellular proteins processed through the full system and 55% for intracellular proteins recovered after lysis.

Cell and Large Particle Filter Based on Acoustic Focusing

The cell filter uses acoustic focusing, an ideal method for size-based separation of particles larger than 2 pm. Using a piezoelectric transducer, we set up acoustic standing waves in a microfluidic channel. These waves produce a force field which moves particles to nodes or antinodes of the acoustic wave depending on the relative compressibility and density between the particle and the suspending liquid. The magnitude of the acoustic forces scales with the volume of the particle providing a natural size cutoff for fractionation, while the node and antinode locations depend on the fluid channel geometry and the acoustic driving frequency. This type of system is well suited as a first-stage fractionation module due to the large, selective transport forces and large sample processing capabilities.

Nucleic Acids Filter Based on Isotachophoresis

The nucleic acid filter leverages isotachophoresis (ITP), an electrophoresis technique which allows for simultaneous separation and preconcentration of target chemical and biological species. ITP uses a discontinuous buffer system consisting of leading (LE) and terminating electrolytes (TE) to simultaneously separate and focus target species into segregated zones according to their respective electrophoretic mobilities. ITP has been widely applied to the separation and preconcentration of nucleic acids.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A microfluidic automated sample preparation apparatus for preparation of a biological sample, consisting of:
   a sample preparation system including a series of modules for automated sample preparation including the following series of modules connected in series including pumps, valves, and electronics to load the sample and pump the sample through the apparatus,
   wherein the first of said series of modules is a microfluidic acoustic focusing filter module,
   wherein the second of said series of modules is a dielectrophoresis bacteria filter module connected to said microfluidic acoustic focusing filter module,
   wherein the third of said series of modules is a dielectrophoresis virus filter module connected to said dielectrophoresis bacteria filter module,
   wherein the fourth of said series of modules is an isotachophoresis nucleic acid filter module connected to said dielectrophoresis virus filter module,
   wherein the fifth of said series of modules is a lysis module connected to said isotachophoresis nucleic acid filter module, and
   wherein the sixth of said series of modules is an isotachophoresis-based nucleic acid filter connected to said lysis module.

2. An apparatus for preparation of a biological sample, consisting of:
   a sample collector for collecting the biological sample;
   a sample preparation system connected to said sample collector; said sample preparation system including a series of modules connected in series including pumps, valves, and electronics to load the sample and pump the sample through the system,
   wherein the first of said series of modules is a microfluidic acoustic focusing filter module,
   wherein the second of said series of modules is a dielectrophoresis bacteria filter module connected directly to said microfluidic acoustic focusing filter module,
   wherein the third of said series of modules is a dielectrophoresis virus filter module connected directly to said dielectrophoresis bacteria filter module,
   wherein the fourth of said series of modules is an isotachophoresis nucleic acid filter module connected directly to said dielectrophoresis virus filter module,
   wherein the fifth of said series of modules is a lyses module connected directly to said isotachophoresis nucleic acid filter module, and
   wherein the sixth of said series of modules is an isotachophoresis-based nucleic acid filter connected directly to said lysis module.

* * * * *